(12) United States Patent
Bijl

(10) Patent No.: US 9,095,099 B2
(45) Date of Patent: Aug. 4, 2015

(54) CONTAINER FOR CULTIVATING BIOLOGICAL MATERIALS

(75) Inventor: Jacob Johannes Bijl, Burgh-Haamstede (NL)

(73) Assignees: VISSER 'S-GRAVENDEEL HOLDING B.V., Kh's-Gravendeel (NL); VITRO PLUS C.V., Ba Burgh-Haamstede (NL)

( * ) Notice: Subject to any disclaimer, the term of this patent is extended or adjusted under 35 U.S.C. 154(b) by 116 days.

(21) Appl. No.: 13/073,053

(22) Filed: Mar. 28, 2011

(65) Prior Publication Data

US 2011/0232189 A1    Sep. 29, 2011

Related U.S. Application Data

(63) Continuation of application No. 11/570,177, filed as application No. PCT/NL2005/000427 on Jun. 10, 2005, now abandoned.

(30) Foreign Application Priority Data

Jun. 10, 2004    (NL) .................................... 1026379

(51) Int. Cl.
*A01G 31/00*    (2006.01)
*A01G 9/10*    (2006.01)
*A01H 4/00*    (2006.01)

(52) U.S. Cl.
CPC ............. *A01G 9/1033* (2013.01); *A01G 9/1026* (2013.01); *A01G 9/1086* (2013.01); *A01H 4/001* (2013.01); *A01G 2009/1053* (2013.01)

(58) Field of Classification Search
CPC ... A01H 4/001; A01G 9/1026; A01G 9/1086; A01G 2009/1053

USPC .............. 435/289.1, 420; 47/59 S, 65.5, 66.1, 47/66.5, 66.6

See application file for complete search history.

(56) References Cited

U.S. PATENT DOCUMENTS 4,912,874 A    4/1990    Taylor
5,119,588 A *  6/1992    Timmis et al. ............. 47/58.1 R (Continued)

FOREIGN PATENT DOCUMENTS

EP    0079046 A    5/1983
EP    0287284 A    10/1988

(Continued)

OTHER PUBLICATIONS

Kanechi et al. "The Effects of Carbon Dioxide Enrichment, Natural Ventilation, and Light Intensity on Growth, Photosynthesis, and Transpiration of Cauliflower Plantlets Cultured in vitro Potoautotrophically and Photomixotrophically." The Journal of the American Scoiety of Horticulture Science 123(2): 176-81. 1998.*

*Primary Examiner* — Michael Hobbs
(74) *Attorney, Agent, or Firm* — Karl Bozicevic; Bozicevic, Field & Francis LLP

(57) ABSTRACT

The present invention relates to a container for cultivating biological material, comprising a solid inert substrate, a growth medium and biological material arranged in or on the substrate, wherein the container is substantially closed, wherein the volume of the container is sterile and wherein the biological material comprises sowing material, and to a method and the use of the container for cultivating biological material.

2 Claims, 1 Drawing Sheet

(56) References Cited

U.S. PATENT DOCUMENTS

| | | | | |
|---|---|---|---|---|
| 6,013,524 | A | * | 1/2000 | Friars et al. ............... 435/420 |
| 6,032,409 | A | | 3/2000 | Obonai et al. |
| 6,427,378 | B1 | * | 8/2002 | Obonai et al. ............... 47/44 |
| 2002/0020673 | A1 | * | 2/2002 | Nohren et al. ............... 210/660 |
| 2004/0029266 | A1 | * | 2/2004 | Barbera-Guillem ....... 435/297.5 |
| 2005/0287660 | A1 | * | 12/2005 | Aubry et al. ............... 435/297.1 |

FOREIGN PATENT DOCUMENTS

| | | |
|---|---|---|
| ES | 551397 | 1/1986 |
| FR | 1551682 A | 12/1968 |
| FR | 2713042 A | 6/1995 |
| JP | 09107799 | 4/1997 |
| WO | WO9113541 A | 9/1991 |

* cited by examiner

CONTAINER FOR CULTIVATING BIOLOGICAL MATERIALS

FIELD OF THE INVENTION

The present invention relates to a container and method for cultivating biological material in container for cultivating biological material, comprising a solid inert substrate, a growth medium and biological material arranged in or on the substrate, characterized in that the container is substantially closed, wherein the volume of the container is sterile and the biological material comprises sowing material, and to the use of the container in the cultivation of biological material.

BACKGROUND OF THE INVENTION

A container for cultivating biological material according to the container for cultivating biological material, comprising a solid inert substrate, a growth medium and biological material arranged in or on the substrate, characterized in that the container is substantially closed, wherein the volume of the container is sterile and the biological material comprises sowing material is known from U.S. Pat. No. 6,032,409.

SUMMARY OF THE INVENTION

In the cultivation of biological material it is important to obtain the highest possible yield. In the case of vegetable material the procedure is generally as follows. Firstly, biological cell material is placed in a first closed, sterile container. This container is generally provided with an agar medium. This first container is placed under conditions such that the biological cell material starts to grow. Once the biological cell material has begun to grow to some extent, the cell material is removed from the agar situated in the first container and transferred to a second container. During this transfer the cell material is washed often so that substantially all the agar is removed. In the case of a large number of plant types the biological cell material is then processed into so-called sowing material. Usual processing methods here are shredding or singulating, although other processing methods are also possible. The thus obtained sowing material is then placed in a second container, which container also comprises an agar medium. Once the sowing material has developed sufficiently, the sowing material is removed from the second container and arranged on or in a solid inert substrate situated in a third container. The developed sowing material is here generally washed with water such that practically all the agar is removed. This final step of removing and washing the developed sowing material takes place manually and thereby has a number of drawbacks. Firstly, the transfer of the developed sowing material is very labour-intensive, which has an unfavourable effect on the cost price of the biological material. Contamination of the sowing material or the developed sowing material with micro-organisms further occurs very easily. This results in the biological material not growing, or growing very poorly. This also has an unfavourable effect on the cost price. In addition, agar medium often still remains on the developed sowing material despite the washing. Finally, when this sowing material is then arranged (manually) on or in a solid substrate, there is a high risk of micro-organisms such as fungi multiplying easily in this residual agar medium. After the container with the solid inert substrate, as a final step the grown sowing material is transferred together with the substrate from this container and into a final container or pot provided with potting compost or the like. The cultivation of biological material thus consists of diverse processing steps and is herein a labour-intensive and relatively expensive procedure.

The present invention has for its object to provide a solution to the above stated problems.

A first aspect of the present invention results in a container for cultivating biological material, comprising a solid inert substrate, a growth medium and biological material arranged in or on the substrate, characterized in that the container is substantially closed, wherein the volume of the container is sterile and the biological material comprises sowing material.

The advantage of such a container is that the penultimate step of transferring the developed sowing material from a second container to a third container with a solid inert substrate no longer has to take place. The above described operations such as the transfer and washing hereby no longer need be carried out. This has a favourable effect on the cost price. Contamination of the sowing material with micro-organisms is further also avoided.

The sowing material is preferably chosen from the group comprising seeds such as vegetable seeds of for instance tomato, cucumber and paprika, seeds of ornamental plants such as Gerbera, Anthurium, Bromelia, Orchid and Spathiphyllum, and seeds of arable crops, shredded and singulated vegetable material, vegetable somatic embryos, fern spores, adventive or axillary shoots or parts thereof. The shredded vegetable material preferably comprises shredded fern parts, ferns, saintpaulia, primula and lily. The adventive or axillary shoots or parts thereof preferably originate from vegetable crops such as tomato, cucumber and paprika. The adventive or axillary shoots or parts thereof further preferably originate from ornamental plants such as Gerbera, Anthurium, Bromelia, Orchid, Spathiphyllum, fern, Syngonium, lily, or from arable crops such as potato. Vegetable somatic embryos preferably used as sowing material are somatic embryos of trees, such as for instance those of coniferous trees (spruce, pine). The present invention is particularly important for this group of sowing material since these are susceptible to infections with undesirable micro-organisms. It is therefore also recommended that the sowing material is sterile. It is noted here that sterile is understood to mean not only an absolute sterility, but also a degree of sterility such as is necessary to allow the sowing material to grow.

The solid inert substrate preferably comprises rockwool, glass wool, coconut fibre, peat, hemp fibres, purane foam, potting compost and/or cellulose wadding or similar substrate. The advantage of these substrates is that they are particularly suitable for cultivating biological material due to their inert properties. In addition, rockwool, glass wool, purane foam and cellulose wadding in particular can be easily sterilized.

The growth medium preferably comprises water, salts (minerals) and/or sugars, such as an agar medium and preferably a liquid or (highly) diluted agar medium. Especially when the $CO_2$ concentration inside the container is relatively high, there are preferably no, or only few, sugars present in the growth medium. The advantage hereof is that the autotrophic growth of the sowing material is encouraged, whereby it ultimately becomes stronger.

At least one side of the container is preferably closed by means of a semi-permeable foil. The advantage hereof is that the container is closed off from the environment, whereby a so-called micro-environment is created. The advantage of such an environment is that the conditions inside the container can be controlled very precisely. The semi-permeable foil plays an important part here, since it can be chosen such that it is for instance permeable to determined gases but not to others (for instance permeable to O2 to the outside but not to $CO_2$). In this manner the conditions inside the space of the container can thus be set such that they are ideal for the biological material for cultivating, such as sowing material.

The volume of the container is preferably provided with a gas mixture with an increased $CO_2$ concentration. The advantage hereof is that the autotrophic growth of the biological material is enhanced.

It is further advantageous when the container is provided with a valve for administering a gas mixture, nutrients and/or growth-stimulating agent, such as a hormone, to the volume of the container. By incorporating a valve in the container the space inside the container can be adjusted to the ideal conditions of the biological material at that moment.

It is further recommended that the sowing material is situated in a carrier preparation. It is preferably situated in a gel, such as a gel on agar basis, in a liquid, likewise for instance on agar basis. The advantage hereof is that the first stage of the growth of the sowing material takes place in the carrier preparation and a subsequent stage takes place in the solid substrate located under the carrier preparation. A further great advantage of the use of a carrier preparation is that the sowing material can be arranged on the solid inert substrate in simple and fully automated manner. This has a favourable effect on the cost price of the biological material, as well as the chance of contamination by micro-organisms. In addition to a carrier substance, the carrier preparation preferably comprises different ingredients which are necessary or advantageous for the growth of the sowing material. Examples of such ingredients are water, salts, sugars and seaweed. The growth medium added to the inert substrate preferably comprises water, salts (minerals) and sugars. It is recommended here that the content of sugars in the inert substrate is lower than in the carrier preparation.

As stated, it is recommended that the carrier preparation comprises agar. The advantage hereof is that it is a very stable medium and that different ingredients such as water, sugars and salts (minerals) can readily be added thereto.

The container is preferably an outer container in which at least one sub-container is placed, wherein the sub-container receives the solid inert substrate with sowing material. The advantage of such a container is that the sub-containers can be provided separately of the container with the inert substrate, the growth medium and the sowing material. It is thus possible to use less complex machines. An additional advantage is that, if one of the sub-containers were to be contaminated with an undesirable micro-organism, it does not spread so quickly over all the other containers. The container preferably comprises between 1 and 500 sub-containers. A second aspect of the present invention relates to a method for cultivating biological material, comprising the steps of:

providing a sterile biological cell material;
placing the cell material in a first closed, sterile container provided with an agar medium and allowing the cell material to grow in this first container;
removing the grown cell material from the first container and dividing thereof into smaller parts to form sowing material,
placing the sowing material in a second container for further growth, characterized by
arranging the sowing material in or on an inert solid substrate, wherein the substrate is accommodated by the second container,
arranging a growth medium in the second container, and closing the second container in sterile manner.

The advantage of the above described method is that the sowing material no longer has to be cultivated first in a second container with an agar medium and then in yet another container with a solid inert substrate therein. According to the invention these two steps take place simultaneously in a container according to the invention. The advantage hereof is that the chance of contamination of the sowing material is reduced. In addition, the developed sowing material no longer has to be removed from the container with agar and washed manually. This has a favourable effect on the cost price of the cultivated biological material.

It is further recommended that, after growing, at least a part of the solid inert substrate with further grown (developed) sowing material is transplanted into a container with a substantially equivalent substrate. The advantage hereof is that the so-called capillary action, i.e. the extraction of moisture and nutrients from the substrate on which the sowing material has developed, is avoided. This has a favourable effect on the quality of the cultivated biological material.

A final aspect of the present invention relates to the use of the above described container in the cultivation of biological material.

The invention will now be described further using the following drawings and examples. These figures and examples serve only by way of illustration of the invention and are in no way intended to limit the scope of the invention.

DETAILED DESCRIPTION OF THE INVENTION

Figure 1:
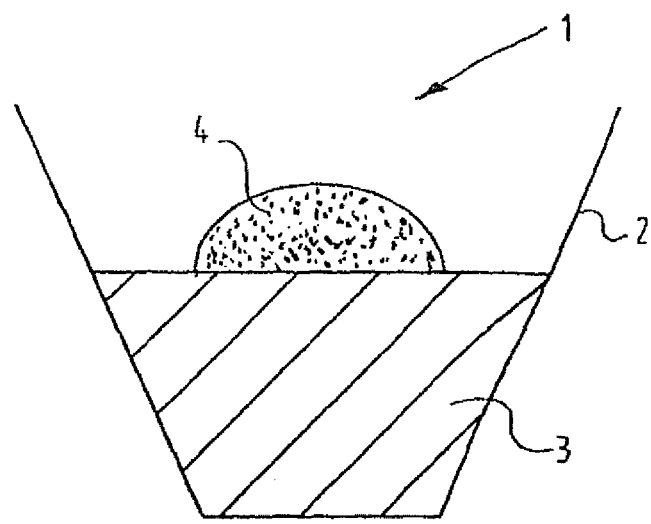
FIG. 1 shows a schematic side view of a container according to the invention.

FIG. 1 shows a side view of a container 1 according to the invention. Within the walls 2 of container 1 is placed an inert solid substrate 3 which is provided with growth medium. A quantity of sowing material in carrier material 4 is arranged on the top side of substrate 3. When the sowing material begins to develop, carrier material 4 is used up and the material continues to grow in substrate 3. Substrate 3 can then be separated from the container and be transferred into a pot with potting soil or similar substrate.

Figure 2:
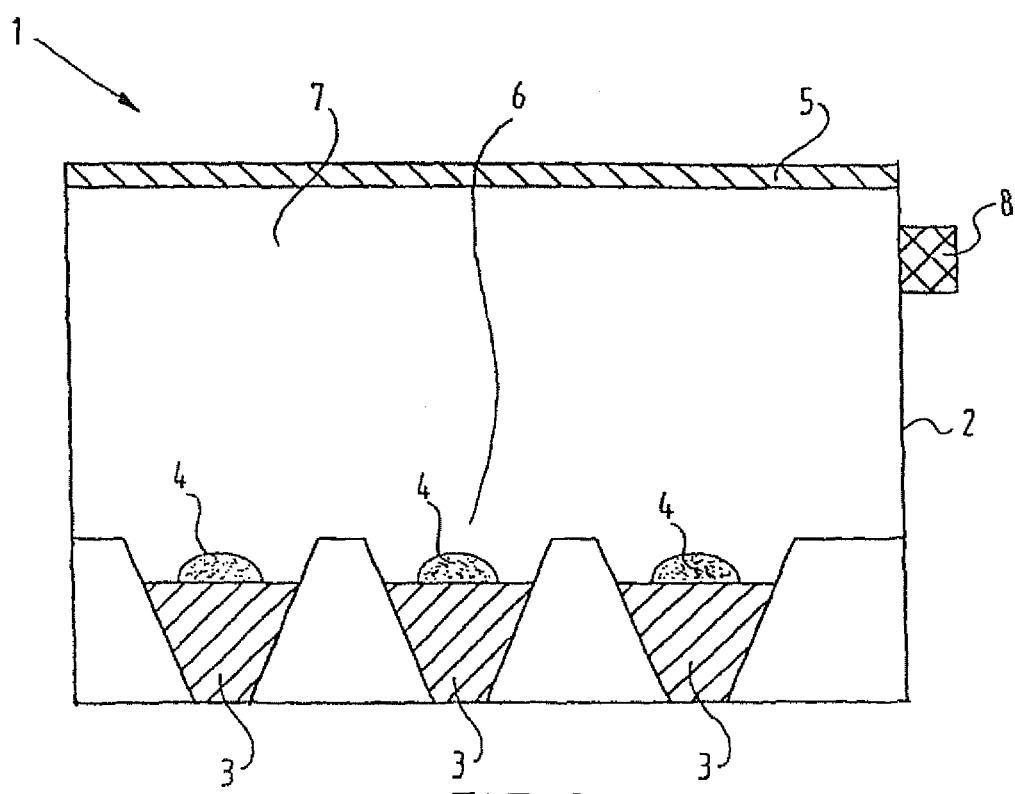
FIG. 2 shows a schematic side view of a container according to the invention provided with a plurality of sub-containers.

FIG. 2 shows a side view of a container 1 according to the invention. Container 1 is provided with a plurality of sub-containers 6 placed in container 1. An inert substrate 3 is arranged in each sub-container 6. A carrier preparation 4 with sowing material therein is arranged on substrate 3. Container 1 is closed along side walls 2 by means of transparent plastic material. The top side of container 1 is closed using a semi-permeable foil 5. This foil 5 ensures that the gas composition of inner space 7 of container 1 has the desired composition and humidity. Foil 5 further ensures that the sowing material does not become contaminated with undesired micro-organisms. To enable the gas composition of inner space 7 of container 1 to be changed a valve 8 is placed against one of the walls 2 of container 1. additional growth medium can however also be added to substrate 3 of sub-containers 6 through this valve 8.

EXAMPLES

Example 1

In a first group 104 sub-containers were placed under sterile conditions in a container according to the invention. The sub-containers were mutually connected on the top side such that they formed a tray. Arranged in the sub-containers was rockwool which was provided with a growth medium. Sowing material in a carrier preparation was arranged on the rockwool. The carrier preparation here comprised agar-agar, water, salts and sugar. The sowing material comprised shredded fern parts of the type *Nephrolepis exaltata* 'Corditas'. The container, the sub-containers, the rockwool and the carrier preparation with sowing material were all sterile. The container was then closed under sterile conditions using a semi-permeable foil (PET 12/PE30). The container with the sowing material therein was incubated for 40 days at 25° C. and at an interval of 16 hours daylight and 8 hours night. The plants were incubated until they were large enough to be transferred into a so-called transplant tray with potting soil. In this transplant tray they were placed in a greenhouse and kept there until they were large enough to be placed in pots.

In a second group a large number (104) of sterile sub-containers were provided with an agar mixture on which sowing material was arranged (shredded fern parts of the type *Nephrolepis exaltata* 'Corditas'). The sub-containers were placed in a sterile container which was closed on one side using a semi-permeable foil (PET 12/PE30). The whole was then incubated in controlled conditions, i.e. for 49 days at 25° C. and a day-night interval of respectively 16 and 8 hours. Once the sowing material had formed sufficient roots, the sowing material was transferred into a so-called transplant tray with potting soil. In this transplant tray they were placed in a greenhouse and kept there until they were large enough to be placed in pots.

Table 1 shows the growth of the plants in a sterile container until they can be transferred to a transplant tray with potting soil.

Table 2 shows the growth of the plants in a non-sterile transplant tray up to the moment the plants can be placed in pots.

Vitro-growth time is understood to mean the time required for the sowing material to grow into a processable plant. Plant size is understood to mean the diameter of the plant at the top. Plant height designates the height of the plant. Root length is understood to mean the length of the roots in the rockwool or in the agar. Rooting time is understood to mean the time necessary to grow into a plant which can be potted. Finally, failure percentage indicates the percentage of sowing material which does not develop into an acceptable plant.

TABLE 1

Growth up to transfer to transplant tray

|  | Group 1 | Group 2 |
| --- | --- | --- |
| vitro growth time | 40 days | 49 days |
| vitro plant size | 15 mm | 11 mm |
| vitro plant height | 15 mm | 10 mm |
| vitro root length | 8 mm | 3 mm |

TABLE 2

Growth up to transfer to pot

|  | Group 1 | Group 2 |
| --- | --- | --- |
| rooting time | 26 days | 34 days |
| vivo plant size | 130 mm | 70 mm |
| vivo plant height | 50 mm | 30 mm |
| vivo root length | 80 mm | 50 mm |
| failure percentage | 0% | 5% |

Table 1 shows clearly that the plants from group 2 need more time to grow before they can be placed in pots. It is further shown that the roots of the plants of group 1 are better developed.

Table 2 clearly shows that the rooting time in the transplant tray with potting soil is markedly shorter in the plants of group 1. This table further also shows that the failure percentage of the second group is much higher than that of the first group.

The invention claimed is:

1. A container for cultivating biological sowing material, comprising:
   a solid inert substrate;
   a growth medium; and
   a biological sowing material in contact with the substrate,
   a gas mixture in the container having an increased $CO_2$ concentration such that autotrophic growth of the biological sowing material is enhanced;
   characterized in that the container is provided with a valve for administering a material selected from the group consisting of a gas mixture, nutrient and a growth-stimulating agent,
   wherein the container is closed, characterized in that the container content is sterile wherein at least one entire side of the container is closed with a semi-permeable foil comprised of polyethylene terephthalate (PET) as a PET 12/PE30 laminate which material is characterized by permeability to oxygen and impermeability to micro-organisms and carbon dioxide, and the sowing material is situated in agar.

2. A container for cultivating biological sowing material, comprising:
   a solid inert substrate comprised of a growth medium; and
   a biological sowing material in a carrier material positioned in a separate layer on top of and in contact with the substrate,
   wherein the container is closed, characterized in that the container content is sterile wherein at least one entire side of the container is closed with a semi-permeable foil comprised of polyethylene terephthalate (PET) which material is characterized by permeability to oxygen and impermeability to micro-organisms and carbon dioxide, and the carrier material comprises agar, water, salt and sugar.

\* \* \* \* \*